US00PP33625P2

(12) United States Plant Patent
Trees

(10) Patent No.: US PP33,625 P2
(45) Date of Patent: Nov. 9, 2021

(54) ***BUDDLEIA* PLANT NAMED 'BUDDAPLAV'**

(50) Latin Name: *Buddleia davidii*
Varietal Denomination: Buddaplav

(71) Applicant: THE CONARD PYLE COMPANY, West Grove, PA (US)

(72) Inventor: Scott C. Trees, Arroyo Grande, CA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 17/130,931

(22) Filed: Dec. 22, 2020

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
CPC ..... A01H 6/00; A01H 5/02
See application file for complete search history.

(56) References Cited

U.S. PATENT DOCUMENTS

PP25,730 P2 7/2015 Trees
PP30,236 P2 2/2019 Wood

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Buddleia* plant, referred to by its cultivar name, 'Buddaplav', is disclosed. The new variety forms attractive light purple colored flowers. Attractive, medium green colored foliage is formed. The growth habit is compact, mounded and the plant has moderate growth vigor. The new variety is well suited for providing attractive ornamentation in the landscape.

1 Drawing Sheet

Botanical/commercial classification:
Latin name: *Buddleia davidii.*
Varietal denomination: 'Buddaplav'.

SUMMARY OF THE INVENTION

The new variety of *Buddleia davidii* plant originated in a controlled breeding program in Guadalupe, Calif. during June 2015. The objective of the breeding program was the development of a series of *Buddleia* cultivars with compact and well-branched habits. The new cultivar was created by cross-pollination wherein two parents were crossed which previously had been studied in the hope that they would contribute the desired characteristics. The female parent (i.e., the seed parent) was an unnamed breeder seedling variety (not patented). The male parent (i.e., the pollen parent) was the 'Boscranz' variety (U.S. Plant Pat. No. 25,730).

The parentage of the new variety can be summarized as follows:

unnamed breeder seedling x 'Boscranz'

The new cultivar was discovered and selected as a single flowering plant from the progeny resulting from the above-stated cross-pollination during July 2016 in a controlled environment in Guadalupe, Calif. Selective study resulted in the identification of a single plant of the new variety.

It was found that the new variety of *Buddleia* plant of the present invention:

(a) forms light purple colored flowers,
(b) displays medium green colored foliage, and
(c) exhibits a moderately vigorous and compact, mounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed breeding seedling (i.e., the seed parent) displays lavender colored flowers and very compact and well-branched growth habit, whereas the new variety provides light purple colored flowers and compact, mounded growth habit. The 'Boscranz' variety (i.e., the pollen parent) displays dark cranberry colored flowers, whereas the new variety displays light purple colored flowers.

The new variety can also be distinguished from other similar varieties that are commercially available. For instance, the new variety of the present invention can readily be distinguished from the 'SMNBDL' variety (U.S. Plant Pat. No. 30,236), as the new cultivar displays sturdier stems and a denser growth habit with new blooms that hide the old blooms as compared to plants of the 'SMNBDL' variety.

The new variety has been found to undergo asexual propagation by terminal stem cuttings. Asexual propagation by terminal stem cuttings in Guadalupe, Calif. since August 2016 has shown that the characteristics of the new variety are stable and are strictly transmissible by such asexual propagation from one generation to another. Accordingly, the new variety undergoes asexual propagation in a true-to-type manner.

The new variety has been named 'Buddaplav'.

The new variety was first offered for sale on Jan. 8, 2020 at Baltimore, Md. by the inventor or by another who obtained the new variety directly or indirectly from the inventor.

BRIEF DESCRIPTION OF THE PHOTOGRAPH

The accompanying photograph shows as nearly true as it is reasonably possible to make the same, in a color illustration of this character, typical specimens of the plant and plant parts of the new variety. Colors in the photograph may differ slightly from the color values cited in the detailed description, which accurately describes the colors of the 'Buddaplav' variety. The plant was grown in one-gallon pot for approximately four months outside at Cochranville, Pa. Plants were pinched once after transplant.

Drawing—illustrates a specimen of the plant displaying the overall growth and flowering habit—side view.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in August 2020 under natural light conditions in Cochranville, Pa. The description is based on the observation of plants produced from cuttings from stock plants and grown in one-gallon containers for approximately four months in an outdoor nursery in Cochranville, Pa. Plants were pinched once after transplant.

Class: *Buddleia* Plant.

Common name: Butterfly bush.

Propagation:

- *Type cutting*.—Terminal stem.
- *Time to initiate roots*.—Approximately 10 to 14 days on average.
- *Time to produce a rooted cutting*.—Approximately 21 to 25 days on average.
- *Root description*.—Fibrous.
- *Rooting habit*.—Freely branching.

Plant:

- *Habit*.—Moderate growth vigor and compact and mounding growth habit.
- *Commercial crop time*.—Approximately 2 months from a rooted cutting to finish in a 1-gallon container on average.
- *Size*.—Approximately 30.0 cm in height from soil level to top of plant plane on average; and approximately 50.0 cm in width on average.

Branches:

- *Branching habit*.—Freely branching, pinching enhances basal branching.
- *Quantity of main branches per plant*.—Approximately 6 on average.
- *Strength*.—Commonly strong, somewhat flexible and becomes woody with age.
- *Size*.—Length: approximately 17.0 cm on average. Diameter: approximately 6.0 mm on average. Length of central internode: approximately 3.5 cm on average.
- *Texture*.—Viscid, densely glandular pubescent.
- *Color*.—Young stems: commonly near Yellow-Green Group 146C. Mature stems: commonly near Greyed-Orange Group 177B.

Foliage:

- *Number of leaves*.—Approximately 32 per branch on average; and approximately 10 per branched lateral stem on average.
- *Fragrance*.—None detected.
- *Form*.—Simple.
- *Arrangement*.—Opposite.
- *Durability to stress*.—Moderate to high.

Leaves:

- *Aspect*.—Primarily perpendicular to stem.
- *Shape*.—General: lanceolate to oblanceolate. Margin: entire to serrulate. Apex: acute. Base: attenuate.
- *Venation*.—Pattern: pinnate, reticulate. Upper surface color on mature foliage: indistinguishable from the upper surface leaf color. Lower surface color on mature foliage: commonly near Greyed-Green Group 191A.
- *Size*.—Length of mature leaf: approximately 7.0 cm on average. Width of mature leaf: approximately 2.0 cm on average.
- *Texture*.—Upper and lower surfaces: pubescent.
- *Color*.—Upper surface of mature foliage: commonly between near Green Group 139A. Lower surface of mature foliage: commonly near Greyed-Green Group 191C.
- *Petiole*.—Shape: rounded, slightly curved. Length: approximately 5.0 mm on average. Width: approximately 3.0 mm on average. Texture: densely pubescent with lanulose hairs. Color: commonly near Yellow-Green Group 144B.

Inflorescence:

- *Quantity*.—Approximately 25 open inflorescences per plant on average, and approximately 100 open flowers per inflorescence at a time, opening from base to apex.
- *Type*.—Terminal panicles, each panicle having about 2 to 4 branches on average; and flowers persistent, facing upward and outward.
- *Shape*.—Conical.
- *Fragrance*.—Moderately strong sweet scent.
- *Depth or height*.—Approximately 7.0 cm on average.
- *Width*.—Approximately 3.5 cm on average.
- *Rachis*.—Strength: strong. Length: approximately 7.0 cm on average at the time flowers begin to open and approximately 13.0 cm at the end of flowering. Diameter: approximately 2.0 mm on average. Texture: pubescent with stellate hairs. Color: commonly near Greyed-Green Group 191B.

Flower:

- *Type*.—Single, salverform.
- *Bud just before opening*.—Shape: oblong. Length: approximately 7.0 mm on average. Diameter: approximately 1.0 mm on average. Texture: glabrous. Color of petals: commonly near Purple-Violet Group N82A.
- *Corolla*.—Shape: rotate, commonly 4 petals arranged in a single whorl. Depth: approximately 3.0 cm on average. Width: approximately 7.0 mm on average.
- *Petals*.—Shape: rotund. Margin: erosulate. Apex: rounded. Length from throat: approximately 3.0 mm on average. Width: approximately 3.0 mm on average. Texture of upper and lower surfaces: glabrous. Color of upper and lower surfaces when first and fully open: commonly near Purple-Violet Group N82B.
- *Corolla tube*.—Length: approximately 8.0 mm on average. Width: approximately 1.0 mm on average. Diameter of throat opening: approximately 1.0 mm on average. Inner surface: texture is lightly pubescent and color is commonly near Yellow-Orange Group 21B. Outer surface: texture is glabrous and color is commonly near Red-Purple Group 71D.

*Calyx*.—Shape: tubular. Length: approximately 4.0 mm on average. Diameter: approximately 1.0 mm on average.

*Sepals*.—Quantity per flower: commonly 4 on average, fused at base. Length: approximately 4.0 mm on average. Width: commonly less than 1.0 mm. Apex: acute. Margin of free portion: entire. Inner surface: Texture: glabrous. Color: commonly near Yellow-Green Group 144C. Outer surface: Texture: moderately pubescent. Color: commonly near Yellow-Green Group 144C.

*Pedicels*.—Strength: strong, flexible. Length: approximately 3.0 mm on average. Diameter: approximately 1.0 mm on average. Texture: densely pubescent with stellate hairs. Color: commonly near Greyed-Green Group 191B.

*Reproductive organs*.—Androecium: Stamen: commonly 4 per flower, completely adnate to corolla. Anther: shape is lanceolate, length is approximately 1.0 mm on average, and color is commonly near Yellow Group 12D. Pollen: amount is moderate and coloration is commonly near Yellow Group 12D. Gynoecium: Pistil: commonly 1 per flower, length is approximately 2.0 mm on average. Stigma: shape is cleft, two-parted, length is approximately 1.0 mm on average. Seed and fruit: none have been observed to date.

Development:

*Blooming*.—Freely flowering under outdoor growing conditions with substantially continuous blooming from late spring through mid-fall.

*Lastingness of individual flower*.—Approximately 5 days on average.

*Tolerance to disease and pest*.—Not observed to date.

The new 'Buddaplav' variety has not been observed under all possible environmental conditions to date. Accordingly, it is possible that the phenotypic expression may vary somewhat with changes in light intensity and duration, cultural practices, and other environmental conditions.

I claim:

1. A new and distinct cultivar of *Buddleia* plant named 'Buddaplav' characterized by the following combination of characteristics:

(a) forms light purple colored flowers, (b) displays medium green colored foliage, and (c) exhibits a moderately vigorous and compact, mounded growth habit; substantially as herein shown and described.

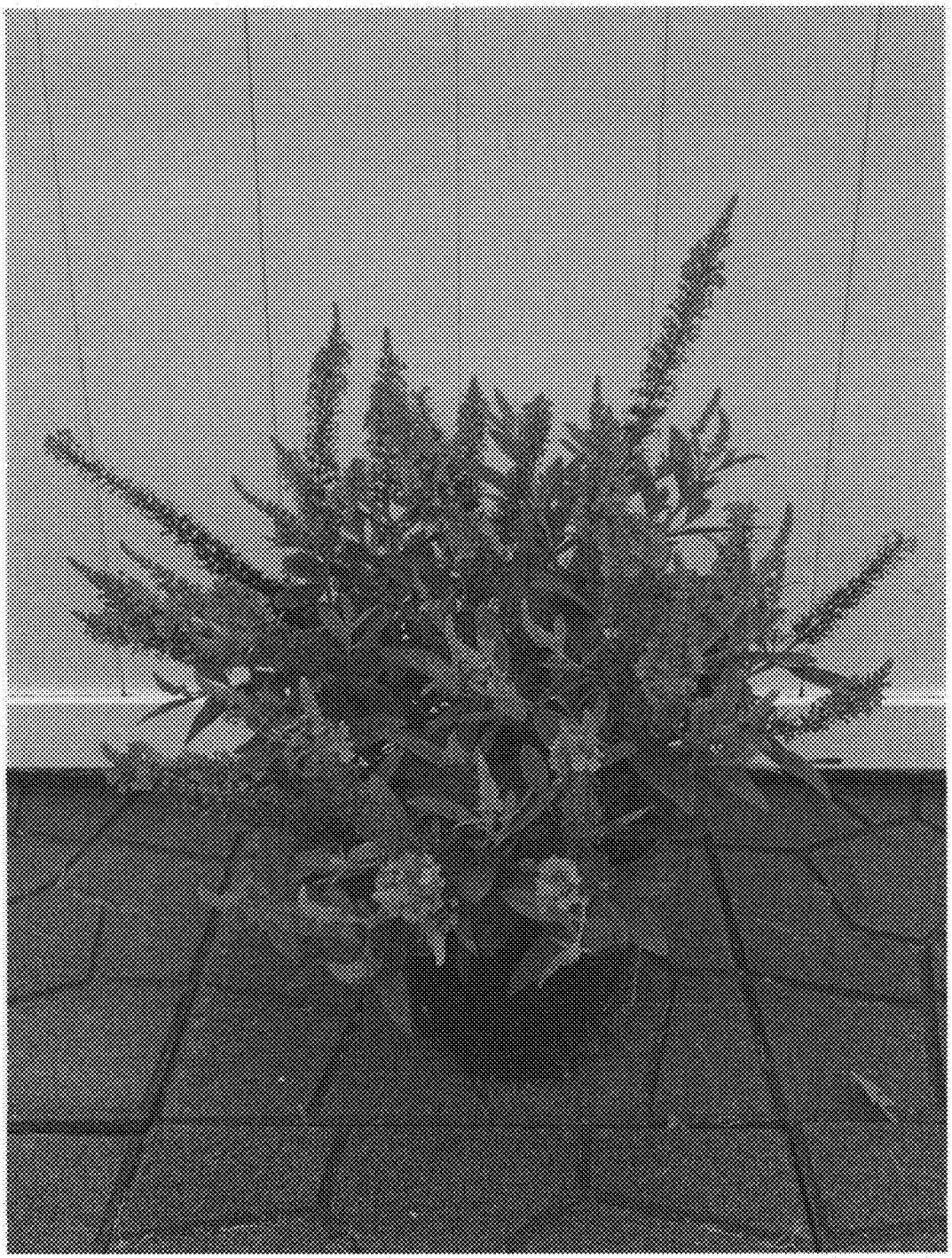

* * * * *